United States Patent [19]

Croce

[11] Patent Number: 4,608,337
[45] Date of Patent: Aug. 26, 1986

[54] HUMAN HYBRIDOMAS AND THE PRODUCTION OF HUMAN MONOCLONAL ANTIBODIES BY HUMAN HYBRIDOMAS

[75] Inventor: Carlo M. Croce, Philadelphia, Pa.

[73] Assignee: The Wistar Institute, Philadelphia, Pa.

[21] Appl. No.: 495,168

[22] Filed: May 17, 1983

Related U.S. Application Data

[63] Continuation of Ser. No. 204,832, Nov. 7, 1980, abandoned.

[51] Int. Cl.$^4$ .................. C12P 21/00; C12N 15/00; C12N 5/00; G01N 33/53
[52] U.S. Cl. .................. 435/68; 435/172.1; 435/172.2; 435/240; 530/387; 436/548; 260/112 B; 935/96; 935/100
[58] Field of Search .................. 435/68, 172, 240, 241, 435/172.1, 172.2, 172.3; 424/88; 436/548; 935/89, 100

[56] References Cited

FOREIGN PATENT DOCUMENTS

| 0014519 | 8/1980 | European Pat. Off. . |
| 0017381 | 10/1980 | European Pat. Off. . |
| 2000186 | 1/1979 | United Kingdom . |
| 2039948 | 8/1980 | United Kingdom . |

OTHER PUBLICATIONS

*The Lancet,* Jun. 11, 1977, pp. 1242-1243.
Kohler et al., *Somatic Cell Genetics,* 1977, vol. 3, pp. 303-312.
Milstein et al., *Immune System: Genetics and Regulation,* pp. 273-275 (ed. Sercarz, Herzenberg & Fox 1977).
Littlefield, *Science,* 1964, vol. 145, pp. 709-710.
Gerhard et al., *European Journal of Immunology,* 1975, vol. 5, pp. 720-725.
Davidson et al., *Somatic Cell Genetics,* 1976, vol. 2, pp. 165-176.
Hall et al., *Proceeding of the National Academy of Sciences USA,* 1979, vol. 76, pp. 2047-2051.
Croce et al., *Science,* 1974, vol. 184, pp. 1288-1289.
Milstein et al., *Antibodies in Human Diagnosis and Therapy,* 1977, pp. 271-284.
Koprowski et al., *Current Topics in Microbiology and Immunology,* 1978, vol. 81, pp. 8-19.
Pontecorvo, *Somatic Cell Genetics,* 1975, vol. 1, pp. 397-400.
Croce et al., *Scientific American,* Jan. 1978, pp. 117-125.
"Researchers at Stanford Develop Cells Creating Human Antibodies," *New York Times,* Jul. 30, 1980, p. 1.
Cicurel et al., *Journal of Immunology,* 1977, vol. 118, pp. 1951-1956.
Davidson et al., *Somatic Cell Genetics,* 1976, vol. 2, pp. 271-280.
Olsson et al., *Proceedings of the National Academy of Sciences USA,* 1980, vol. 77, pp. 5429-5431.
Sekiguchi et al., *Chemical Abstracts,* 1975, vol. 82, p. 85 (ab. 39133p).
Croce et al., *Proceedings of the National Academy of Sciences USA,* 1979, vol. 76, pp. 3416-3419.
Koprowski et al., *Proceedings of the National Academy of Sciences USA,* 1977, vol. 74, pp. 2985-2988.
Welsh, *Nature,* 1977, vol. 266, p. 495.
Croce et al., *European Journal of Immunology,* 1980, vol. 10, pp. 486-488.
Kohler et al., *Nature,* 1975, vol. 256, pp. 495-497.
Kohler et al., *European Journal of Immunology,* 1976, vol. 6, pp. 511-519.
Galfre et al., *Nature,* 1977, vol. 266, pp. 550-552.
Croce, C. M. et al., *Proc. Natl. Acad. Sci. USA,* vol. 76, No. 7, 1979, pp. 3416-3419.
Olsson, L. et al., *Proc. Nat'l. Acad. Sci. USA,* vol. 77, No. 9, 1980, pp. 5429-5431.
Sekiguchi, F. et al., Chemical Abstracts, 1975, vol. 82, No. 6, Abstract #39133p, p. 85.

*Primary Examiner*—Robert J. Warden
*Assistant Examiner*—Jeremy Jay
*Attorney, Agent, or Firm*—Banner, Birch, McKie & Beckett

[57] ABSTRACT

The present invention provides a stable, continuous human myeloma cell line which is capable of hybridization with antibody-producing cells of humans and other animals, the cell line being a mutant of GM 1500 human B cells and being deficient in hypoxanthine phosphoribosyltransferase. The invention also comprises processes for the production of hybrid cells employing the stable, HPRT-deficient human myeloma cell line, and processes for the production of antibodies employing such hybrid cells.

20 Claims, No Drawings

HUMAN HYBRIDOMAS AND THE PRODUCTION OF HUMAN MONOCLONAL ANTIBODIES BY HUMAN HYBRIDOMAS

The invention described herein was made in the course of work under a grant or award from the Department of Health, Education and Welfare.

This is a continuation of application Ser. No. 204,832 filed Nov. 7, 1980, now abandoned.

DESCRIPTION OF THE INVENTION

This invention relates to antibody culture and in particular the production of antibodies by living cells.

The production of antibodies specific for the antigenic determinants of viruses, tumors and foreign agents is of importance both for immunotherapy and for medical research.

Monoclonal antibodies for antigenic determinants have been produced in vitro in cultures of spleen cells infected with a virus, as illustrated by the Epstein-Barr technique. Antibodies have also been produced using fused cell hybrids, or hybridomas, between mouse spleen cells and mouse myeloma cells; see U.S. Pat. Nos. 4,172,124 and 4,196,265. Fused cell hybrids of BALB/c mouse spleen cells and BALB/c mouse myeloma cells have also been described in the literature by Kohler et al in *Nature* Vol. 256, 495–497 (1975), and in *Eur. J Immunol.*, Vol. 6, 511–519 (1976). The spleen cells used to produce these hybrids were taken from mice immunized with sheep red blood cells. Other articles disclosing the production of fused cell hybrids of animal spleen cells and animal myeloma cells include Milstein et al in *Nature*, Vol. 266, 550–552 (1977); Koprowski et al in *Proc. Nat. Acad. Sci.*, Vol. 74, 2985–2988, (1977) and Welsh in *Nature*, Vol. 266, 495 (1977).

The hybridoma technology has been shown capable of yielding satisfactory antibody production rates. However, the antibodies produced by hybridomas consisting of somatic cell hybrids between antibody producing spleen cells and myeloma cells of a BALB/c mouse are necessarily foreign bodies when injected into a human. Hence, the natural human immune response system manufactures antibodies to combat the hybridoma-produced antibodies after their first introduction into the human body. Repeated injections of such antibodies may lead to shock.

Some human chromosomes are normally lost in fusing human lymphocytes with mouse myeloma cells to form mouse-human hybridomas. Such hybrids must retain both of the two human chromosomes that carry the rearranged genes for the human light and heavy immunoglobulin chains in order to be effective. Hence, it is difficult to obtain interspecies hybridomas that secrete human antibodies.

It is advantageous to provide a hybridoma cell formed by fusing a human myeloma cell with a human lymphocyte. Such a hybridoma cell may produce human antibodies with less risk of shock upon repeated injection into a human. However, human myeloma cells do not usually fuse well with human lymphocytes.

It is an object of the present invention to provide a human myeloma cell line which is stable, may be cultured and subcultured indefinitely, and is capable of hybridization with human lymphocytes and with lymphocytes from other animals, to form stable fused cell hybrids.

It is a further object of the present invention to provide a method of producing hybridomas from human myeloma cells, the hybridomas being capable of expressing useful antibodies which are acceptable by the human immune response system.

It is also an object of the present invention to provide a method of producing antibodies of use in treating human diseases, whereby the antibodies produced are acceptable by the human immune response system.

In accordance with the present invention, a composition comprising a stable, continuous human myeloma cell line is provided, which is capable of hybridization with antibody-producing cells of humans and other animals, said cell line being a mutant of GM 1500 human B cells and being deficient in hypoxanthine-phosphoribosyltransferase (HPRT).

In one embodiment of this invention, processes for the production of hybrid cells employing the stable, HPRT-deficient human myeloma cell line of this invention are provided.

In another embodiment, processes for the production of antibodies employing such hybrid cells are provided.

This invention provides, inter alia, methods of producing new cell lines which are genetically stable, can be cultivated and subcultivated indefinitely and produce large amounts of antibodies against viruses, tumors and foreign agents, and their antigenic determinants. These cell lines are fused cell hybrids of (a) a stable, HPRT-deficient human myeloma cell line, i.e., a malignant cell line derived from a primary tumor of bone marrow, and (b) antibody-producing lymphocytes, such as those of the spleen or lymph nodes, or peripheral lymphocytes. A particularly preferred cell line is a fused hybrid between human peripheral lymphocytes or spleen cells, and human myeloma cells. These cell lines can be maintained substantially indefinitely in a culture medium such as hypoxanthine-aminopterin-thymidine (HAT) selective medium, and may continue indefinitely to produce antibodies specific for antigenic determinants.

The myeloma cells of the invention were derived from the GM1500 human B cell line, which cell line was derived from a patient with multiple myeloma. The GM 1500 human B cell line is available from the Human Genetic Mutant Cell Repository, Institute for Medical Research, Camden, N.J.

The GM 1500 myeloma cells were treated with ethyl methyl sulfonate to promote the mutation rate thereof, and selected for HPRT (hypoxanthine phosphoribosyltransferase) deficiency in medium containing 6-thioguanine at a concentration of about 30 micrograms/ml (the basic selection technique is described in *Nature*, Vol. 256, 495–497 (1975)). This process kills most of the myeloma cell; human B cells normally die in 6-thioguanine-containing medium. Moreover, even among the surviving cells, most are not capable of hybridization with lymphocytes.

Two publications have disclosed the hybridization of GM 1500 human B myeloma cells with non-human myeloma cells. The GM 1500 cells were not subjected to mutagen treatment or any selection process prior to fusing in the procedures disclosed in these articles. These articles are: Croce et al in *Proc. Nat. Acad. Sci. U.S.A.*, Vol. 76, 3416–3419 (1974) and Croce et al in *Eur. J. Immunol.*, Vol. 10, 486–488 (1980).

While ethyl methyl sulfonate may be advantageously employed as the mutagen in the above-described procedure, it will be understood that any other mutagen known to one skilled in the art may be employed to mutate the GM 1500 human B cells, as long as the agent does not otherwise adversely affect the cells.

The mutagen treatment and selection process yielded two "survivors", enabling the propagation of modified, stable, HPRT-deficient myeloma cell lines. The two survivors were designated as GM 1500 6TG-A1-1 and GM 1500 6TG-A1-2. The two survivors, which appear to be functionally interchangeable, form continuous cell lines which are deposited at the American Type Culture Collection (ATCC), 12301 Parklawn Drive, Rockville, Md., under access numbers CRL-8032 and CRL-8038, respectively. These myeloma cell lines have the distinctive characteristic that they are capable of hybridization with human lymphocytes, as well as with lymphocytes of other animals. These cells secrete IgG (gamma-2,K immunoglobulin) as did the parental GM 1500 cells, and are Epstein-Barr Virus Nuclear Antigen positive. The cells were maintained in Eagle's minimum essential medium (MEM) (Rosewell Park Memorial Institute (RPMI) 1640 medium could alternatively be used) containing 10% fetal calf serum. The growth of the myeloma cells is inhibited by the selective hypoxanthine-aminopterin-thymidine medium. This medium is disclosed in *Science*, Vol. 145, 709–710 (1964). The remainder of this discussion refers to GM 1500 6TG-A1-2 cells; the GM 1500 6TG-A1-1 cell line could alternatively be employed.

The lymphocytes used may be any lymphocytes from a human individual found to express the desired antibodies. It is also possible to stimulate human lymphocytes in vitro to express the desired antibodies. For example, lymphocytes may be taken from a patient contaminated with an active virus such as rabies, influenza, measles, vaccinia, polio, etc. However, it is to be understood that these are merely examples; lymphocytes expressing antibodies which attack other viruses, or nonviral antigens such as pollen, may also be used. Preferably, the lymphocytes are peripheral lymphocytes separated from a patient's blood, or spleen cells.

In one embodiment of the invention, heparinized blood plasma from a human patient suffering from Subacute Sclerosing Panencephalitis (SSPE), a measles virus infection of the brain, was used as the lymphocyte source. In order to verify the presence of anti-SSPE lymphocytes in this blood plasma, a sample of serum was diluted 1:10,000,000 with phosphate buffer and was found to bind using radioimmunoassay (RIA) to measles-infected target cells. These data as well as evidence of histological lesions of the brian typical of the disease confirmed the clinical diagnosis of SSPE.

A 10 ml sample of heparinized blood plasma from this patient was taken and a suspension of Ficoll-purified lymphocyte cells was prepared in the manner taught by Gerhard et al, Eur, J. Immunol., 5, 720–725 (1975). Red blood cells were lysed by incubation of the blood sample for 15 minutes at 4° C. in $NH_4Cl$ (0.83%). The resulting cell suspension was washed by one centrifugation (800×g) through heat-inactivated calf serum and one centrifugation in protein-free medium (RPMl 1640, buffered with 7.5 mM HEPES, pH 7.2).

Production of hybrids was accomplished by mixing about ten million modified, HPRT-deficient myeloma cells of the invention with one to ten million lymphocytes. The cell mixture was centrifuged at 800×g and the cells were resuspended for fusion in a 50% solution (w/v) of polyethylene glycol-1000 (PEG) diluted in minimum essential medium (MEM) without serum. Following fusion procedures taught by Davidson et al, *Somat, Cell Genet.* 2, 175–176, the polyethylene glycol was diluted first by MEM without serum and then by MEM with serum before the cells were seeded in wells of Linbro plates in hypoxanthine-aminopterin-thymidine selective medium. The cultures were incubated at 37° C. in an atmosphere of 95% air/5% $CO_2$ and every 7 to 10 days the culture medium was partially replaced by fresh (HAT) medium (½ to ⅓).

Fifteen to twenty-one days after incubation of cultures produced by fusion of lymphocytes with myeloma cells, cell growth was observed in twenty out of twenty-four wells. All growth in HAT medium is indicative of successful hybridization between lymphocytes and myeloma cells. These cells were propagated continuously in HAT medium and were cloned in microplates (Linbro) by limiting dilution. Each independent clone (derived from an independent well) was then tested for the expression of human immunoglobulin chains and for the ability to immunoprecipitate measles virus protein. The hybridomas were found to secrete IgM specific for measles virus nucleocapsids, as further shown below.

The specificity of the antibodies for measles virus was determined using immunoprecipitation and 10% SDS-polyacrylamide gel electrophoresis techniques well known in the art. (SDS is an abbreviation for sodium dodecyl sulfate). Generally, cell cultures were labelled with 100 microcuries of $^3H$-leucine (70 curies per millimole) per milliliter of solution by exposure thereto for 12 hours. The human immunoglobulin chains were then immunoprecipitated with rabbit antihuman immunoglobulin antisera according to established procedures. The immunoprecipitated labelled human immunoglobulin chains were then separated by conventional 10% SDS-polyacrylamide gel electrophoresis.

A comparison was made between (1) immunoprecipitates of the immunoglobulin produced by GM 1500 6TG-A1-2 cells following reaction with an antihuman gamma antiserum; (2) immunoprecipitates of immunoglobulin chains secreted by human-human hybridomas (obtained in the fusion procedure described above) following reaction with antihuman mu antiserum; and (3) immunoprecipitates of immunoglobulin chains secreted by a human-human hybridoma following reaction with antihuman mu and gamma chain-specific antisera, using the electrophoretic separation techniques explained above. The purpose of this comparison was to demonstrate that the human-human hybridomas produced according to the invention express both gamma and mu human immunoglobulin chains.

Six hybrid cell clone samples were tested by immunoprecipitation of the immunoglobulins secreted by the hybrids with rabbit anti-mu-antiserum (IgGL). All hybrids expressed the human mu immunoglobulin chain. Some of these hybridomas also expressed a light immunoglobulin chain that migrated differently from the light chain expressed by the GM 1500 6TG-A1-2 myeloma clone. One of these hybridoma clones did not have the ability to produce the light immunoglobulin chain expressed by the GM 1500 6TG-A1-2 cells. The hybridoma culture fluid which was immunoprecipitated with both antihuman mu and antihuman gamma chain rabbit antiserum expressed two heavy immunoglobulin chains, the gamma chain of the GM 1500 6TG-A1-2 parent and the mu chain of the human SSPE (Subacute Sclerosing Panencephalitis) B cell parent.

Another comparison was made using polyacrylamide gel electrophoresis to determine the specificity of the antibodies expressed by the hybridomas of the invention for measles virus antigen. Two samples of hybridoma culture media were compared with two controls. The controls were (1) serum obtained from a human patient recovering from an infection of atypical measles, and (2) culture fluid from the GM 1500 6TG-Al-2 human cell line. Serum from a patient having had atypical measles was chosen to test the cross-effectiveness of the measles virus antibodies. The results of the comparison were obtained using conventional analytical techniques. The procedures used in the immunoprecipitation were as follows: (1) lysates of measles virus-infected CV1 cells labelled with $^{35}$S-methionine were used as antigen; (2) aliquots (25 microliters) of the antigen were mixed with aliquots (100 microliters) of concentrated culture fluid and incubated at about 37° C. for 90 minutes and then at 4° C. for about 4 hours; (3) aliquots (25 microliters) of rabbit total antihuman antibody were then added; (4) the incubations were repeated; (5) the precipitated polypeptides were collected by centrifugation in an Eppendorf centrifuge for 20 minutes at 10,000 rpm; (6) the visible pellet recovered was suspended in phosphate buffer and washed three times; (7) the pellet was suspended in lysis buffer and boiled for three minutes; (8) the resulting solutions were electrophoresed on 10% SDS-polyacrylamide gel under conditions described in Hall et al, *Proc. Nat. Acad. Sci. U.S.A.*, Vol. 76, 2047–2051, (1979). After fluorography, the dried gel was exposed to Cronex X-ray film.

The culture fluids from the hybridoma cultures precipitated the virus NP polypeptide and varied amounts of its cleavage fragments. The antibodies in the culture fluids are thus specific for a single polypeptide, NP, which is the major structural polypeptide of the virus nucleocapsid, and the primary measles virus antigen.

Another comparison was made using SDS-polyacrylamide gel electrophoretic analysis, between (1) the measles virus polypeptides precipitated by culture fluid (unconcentrated) from a hybridoma subclone, obtained by limiting dilution, and (2) the virus polypeptides precipitated by the same atypical measles serum as used above. The results confirm the specificity of the antibodies in the culture fluid of the hybridoma clone, as the subclone thereof precipitates the NP polypeptide with activity comparable to that of the parental hybridoma clone.

The cell line produced by fusing the stable, HPRT-deficient human myeloma cell line of the invention with human antibody-producing lymphocytes, as exemplified by the anti-SSPE lymphocytes used in the above embodiment of the invention, is a hybrid culture displaying characteristics of both the normal lymphocytes and the parental myeloma cells, and appears to be derived from a single fusion event. The cells are hybrid in nature because:

(a) The hybrid cell line has been grown for several months in selective HAT medium which inhibits the growth of the parental myeloma cells but not of the normal lymphocytes which, in turn, would probably not survive for more than 4 to 5 weeks in vitro;

(b) The number of chromosomes in the hybrid cells is close to the sum of that of the normal lymphocytes and parental myeloma cells;

(c) The hybridoma produces new immunoglobulin chains such as mu and light chains; and (d) The hybrid produces specific antibodies, whereas the parental myeloma cells do not produce such antibodies. Additionally, the rate of production of such antibodies is greater than observed in cultures of non-hybridized lymphocytes.

Similar procedures may be carried out by one skilled in the art using other lymphocytes, including human lymphocytes which express other antibodies, and lymphocytes from other animals. As an alternative to growing hybridomas in vitro, hybridoma cells may be injected into an immunosuppressed animal such as a nude mouse for culture in vivo.

The antibodies produced by the hybrids can be recovered using standard techniques and may be used in analytical medical research for identification of antigens in blood samples and culture media. The antibodies are substantially homogeneous and are highly specific to the target antigen. A supply of various homogeneous antibodies, each highly specific to a particular antigen, permits researchers to rapidly determine the specificity of an antigen and/or characterize antigens. In addition, the antibodies can be administered to diseased humans to assist in combating diseases.

While the preferred embodiments of this invention have been discussed herein, those skilled in the art will appreciate that changes and modifications may be made therein without departing from the spirit and scope of this invention, as defined in and limited only by the scope of the appended claims.

I claim:

1. A composition comprising a stable, continuous human myeloma cell line which is capable of hybridization with antibody-producing cells of humans and other animals to form a stable, fused cell hybrid capable of producing said antibody, said cell line being a mutant of GM 1500 human B cells which is deficient in hypoxanthine phosphoribosyltransferase.

2. The composition of claim 1 wherein the cell line is the cell line deposited as ATCC No. CRL-8032.

3. The composition of claim 1 wherein the cell line is the cell line deposited as ATCC No. CRL-8038.

4. In a process for producing a hybrid cell line by fusing an antibody-producing cell and a myeloma cell to provide an antibody-producing fused cell hybrid, the improvement comprising employing a myeloma cell which is a hypoxanthine phosphoribosyltransferase-deficient mutant of a GM 1500 human B cell.

5. The process of claim 4 wherein the myeloma cell is taken from a continuous cell line which is produced by treating GM 1500 human B cells with ethyl methyl sulfonate to promote the mutation rate of the cells, and then selecting the cells with 6-thioguanine for hypoxanthine phosphoribosyltransferase-deficiency.

6. The process of claim 4 wherein the myeloma cell is obtained from the continuous cell line deposited at the ATCC under access number CRL-8032.

7. The process of claim 4 wherein the myeloma cell is obtained from the continuous cell line deposited at the ATCC under access number CRL-8038.

8. The process of claim 4 wherein the fused cell hybrid is cultured and antibodies produced by the cell hybrid are collected.

9. The process of claim 8 wherein said hybrid is cultured in vitro.

10. The process of claim 8 wherein said hybrid is cultured in an immunosuppressed animal.

11. The process of claim 8 wherein said hybrid is cultured in a medium containing hypoxanthine-aminopterin-thymidine.

12. The process of claim 4 wherein said antibody-producing cell is a lymphocyte selected from the group consisting of spleen cells, lymph node cells and peripheral lymphocytes.

13. The process of claim 12 wherein the antibody-producing cell is a peripheral lymphocyte.

14. The process of claim 4 wherein the antibody-producing cell is obtained from a human infected with a virus.

15. The process of claim 14 wherein the virus is selected from the group consisting of rabies, measles, influenza, vaccinia and polio.

16. The process of claim 15 wherein the virus is measles.

17. A fused cell hybrid of (a) a mutant of GM-1500 human myeloma cell line sensitive to hypoxanthine-aminopterin-thymidine medium and (b) an antibody-producing lymphocyte.

18. The fused cell hybrid of claim 17 wherein said myeloma cell line is the cell line deposited as ATCC No. CRL-8032.

19. The fused cell hybrid of claim 17 wherein said myeloma cell line is the cell line deposited as ATCC No. CRL-8038.

20. The fused cell hybrid of claim 17 wherein the antibody-producing lymphocyte is a human lymphocyte.

* * * * *